United States Patent [19]

Cerretti et al.

[11] Patent Number: 5,266,311
[45] Date of Patent: Nov. 30, 1993

[54] BOVINE INTERLEUKIN-1α

[75] Inventors: Douglas P. Cerretti; Charles R. Maliszewski; Michael Schoenborn, all of Seattle, Wash.

[73] Assignee: Immunex Corporation, Seattle, Wash.

[21] Appl. No.: 813,235

[22] Filed: Dec. 23, 1991

Related U.S. Application Data

[60] Continuation-in-part of Ser. No. 432,262, Nov. 3, 1989, abandoned, which is a division of Ser. No. 55,108, May 28, 1987, Pat. No. 4,894,333.

[51] Int. Cl.$^5$ .............. A61K 45/05; A61K 37/66; A01N 37/18; C07K 3/00; C12P 21/02; C12P 19/34
[52] U.S. Cl. .................. 424/85.2; 424/85.7; 514/2; 530/350; 435/69.52
[58] Field of Search .......... 435/69.52, 91, 240.2; 530/350; 424/85.2, 85.7; 514/2

[56] References Cited

U.S. PATENT DOCUMENTS

| | | | |
|---|---|---|---|
| 4,518,584 | 5/1985 | Mark | 424/85 |
| 4,879,374 | 11/1989 | Cerretti | 536/27 |
| 4,894,333 | 1/1990 | Cerretti | 435/69.52 |
| 4,963,354 | 10/1990 | Shepard | 424/85.1 |

FOREIGN PATENT DOCUMENTS 0200986 11/1986 European Pat. Off.

OTHER PUBLICATIONS

Oppenheim et al. "There is more than one interleukin 1", *Immunol. Today* 7:45 (1986).
Durum et al. "Interleukin 1: An Immunological Perspective", *Ann. Rev. Immunol.* 3:263 (1985).
March et al. "Cloning, Sequence and Expression of Two Distinct Human Interleukin-1 Complementary DNAs", *Nature* 315:641 (1985).
Gubler et al., "Recombinant Human Interleukin 1α: Purification and Biological Characterization", *J. Immunol.* 136:2492 (1986).
Tocci et al., "Expression in *Escherichia Coli* of Fully Active Recombinant Human" IL-1β: Comparison with Native Human IL-1β, *J. Immunol.* 138:1109 (1987).
Lomedico et al., "Cloning and Expression of Murine Interleukin-1 cDNA in *Escherichia Coli*", *Nature* 312:458 (1984).
Saklatvala et al., "Pig Interleukin 1", *J. Exp. Med.* 162:1208 (1985).
Banks et al., "Stimulation and killing of bovine mononuclear leukocytes by bacterial lipopolysaccharide" (endotoxin), *Am. J. Vet. Res.* 46(7):1568 (Jul. 1985).
Lederer and Czuprynski, "In vitro production and partial purification of bovine interleukin 1", (abstr.) 42(5):569 (1987).
Staruch and Wood, "The Adjuvanticity of Interleukin 1 In Vivo", *J. Immunol.* 130(5):2191 (1983).
Cerretti et al. "Cloning, sequence, and expression of bovine interleukin 2", *Proc. Natl. Acad. Sci. USA* 83:3223 (1986).
Maniatis et al., *Molecular Cloning: A Laboratory Manual*, Cold Spring Harbor Laboratory, C.S.H., New York, pp. 404-433 (1982).
Yang et al., "Human IL-3 (Multi-CSF): Identification by Expression Cloning of a Novel Hematopoietic Growth Factor Related to Murine IL 3", *Cell* 47:3 (1986).
Cohen et al., "Cloning and Expression of the Rat Interleukin-3 Gene", *Nucl. Acids Res.* 14:3641 (1986).
Maliszewski et al., "Cloning, Sequence and Expression of Bovine Interleukin-1", *J. Leukocyte Biol.* 42:408 (Oct. 1987).
Maliszewski et al., "Cloning, Sequence and Expression of Bovine Interleukin-1α and Interleukin 1β Complementary DNAs", *Mol. Immunol.* 25(5):429 (1988).
Mastro et al., "DNA Synthesis and Production of Interleukin 1 by Lymph Node Macrophages in Culture", *J. Leukocyte Biol.* 39(1):63 (1986).

*Primary Examiner*—Joan Ellis
*Attorney, Agent, or Firm*—Scott G. Hallquist; Stephen L. Malaska; Charlene A. Launer

[57] ABSTRACT

Cloning and expression of DNA segments encoding bovine IL-1α, and processes for producing purified bovine IL-1α as a product of recombinant cell culture, are disclosed.

10 Claims, 2 Drawing Sheets

FIGURE 1

```
   1  GAGAGGGAGC CAGTCATCTC ATTGTTGCTA GCTCGGTTCA GCAAAGAAGT
  51  GAAGATGGCC AAAGTCCCTG ACCTCTTTGA AGACCTGAAG AACTGTTACA
 101  GTGAAAATGA AGACTACAGT TCTGAAATTG ACCACCTCTC TCTCAATCAG
 151  AAGTCCTTCT ATGATGCAAG CTATGAGCCA CTTCGTGAGG ACCAGATGAA
 201  TAAGTTTATG TCCCTGGATA CCTCGGAAAC CTCTAAGACA TCCAAGCTTA
 251  GCTTCAAGGA GAATGTGGTG ATGGTGGCAG CCAGTGGGAA GATTCTGAAG
 301  AAGAGACGGT TGAGTTTAAA TCAGTTCATC ACCGATGATG ACCTGGAAGC
 351  CATTGCCAAT AATACAGAAG AAGAAATCAT CAAGCCCAGA TCAGCACATT
 401  ACAGCTTCCA GAGTAACGTG AAATACAACT TTATGAGAGT CATCCACCAG
 451  GAATGCATCC TGAACGACGC CCTCAATCAA AGTATAATTC GAGATATGTC
 501  AGGTCCATAC CTGACGGCTA CTACATTAAA TAATCTGGAG GAGGCAGTGA
 551  AATTTGACAT GGTTGCTTAT GTATCAGAAG AGGATTCTCA GCTTCCTGTG
 601  ACTCTAAGAA TCTCAAAAAC TCAACTGTTT GTGAGTGCTC AAAATGAAGA
 651  CGAACCCGTC TTGCTAAAGG AGATGCCTGA GACACCCAAA ATCATCAAAG
 701  ATGAGACCAA CCTCCTCTTC TTCTGGGAAA AGCATGGCTC TATGGACTAC
 751  TTCAAATCAG TTGCCCATCC AAAGTTGTTT ATTGCCACAA AGCAAGAAAA
 801  ATTGGTGCAC ATGGCAAGTG GGCCGCCCTC GATCACTGAC TTTCAGATAT
 851  TGGAAAAATA GCCTTGACTG TGCACTCTAC TTACTTGTAA AGTGGTGACC
 901  ATCCGTATGT ACTATGTACA TGAAGGAGTC GAGCCCCTTC ACTGTTAGTC
 951  ACTCGCTGAG CATGTGCTGA GCTTTTGTAA TTCTAAATGA ATGTTACTC
1001  TCTTTGTAAG AGAGAACACC AAACGCTCCA ACACTAACAT ATAATGTTGC
1051  TTGTTATTTA CCGAACACCC TATACTTTGC AAAGTACCAA TCAATTTAAT
1101  TATTATTCTG CACAATAATC TTGGGAGGAC TGAGGCTACT ATCTGTGGCT
1151  ACAAAAGGTT CTTTCCATAT TATAGATGAG TAAACTAAGG CATAAGAATA
1201  CTAATACCCA TGACAGCAGT TGGAATAAGC CGTGGACACA CAATTTCATT
1251  CCAACTGCTC AGCTTCTACT TTTAAGCCAC TGATGGACCC TTTATCAAAT
1301  ACTATAAGTT TCTGGGGTCT CAGTTTGCTG CTGCTGCTAA GTCACTTCAG
1351  TCATGTCCAA CTCTGTGCGA CCCCATAGAC GGCAGCCCAC CAGGCTCCGC
1401  AGTCCCTGGG ATTCTCCAGG CAAGAACACT GGAGTGGGTT GCCAATTTCC
1451  TTCTCCAATG CATGAAGTGA AAAGTGAAAG TGAAGTTGCT CAGTCATGTC
1501  CGACTCTTAG CGACCCCATG GACTGCAGCC TACCAGGCTC CCTCTGTCCA
1551  TGGGATTTTC CAGGCAAGAG TACTGGAGTG GGTGCCCAC TTGCCCTTCT
1601  CCCGGGGTCT CAGTTTGACC ATCTTCAAAA TCAGGGTAAT GATGACTATA
1651  GCCCTCCTAC CTCAACAGTA TTTTATGCCA ATGAGTTCAT TTAAGTAAAA
1701  TTTTCTTGA AGCTGAGCCT CAAGAAGAAT GCAAAGCATG AAATGTTATT
1751  TTAAGTTATT ATTTATATGC ATATATATTT ATAAGCATTA TTTCTAAGAT
1801  ATTATTATTA TTTATAACAT ATTATTATAT TTATGGCAAT TCCTTGCAAT
1851  GTGTGAGTAT GACCAGGTAT CTTCAATAAT AGTAGACAGT GTTTTCTAGG
1901  CTGAGTAAGT CCGAGTACTA ACCGGCACTT TGGTTCAAAG TGCCTTTTCC
1951  ATTGTCATGA ACTTCTGTAT TCCAGTACCT GGGAGCCCTG TGATTATGAT
2001  AATAAATTTA TATTAATTGC CCTGTTAAAA AAAAAAAAAA AAAAAAAAA
```

FIGURE 2

```
ATG GCC AAA GTC CCT GAC CTC TTT GAA GAC CTG AAG AAC TGT TAC AGT    48
Met Ala Lys Val Pro Asp Leu Phe Glu Asp Leu Lys Asn Cys Tyr Ser    16

GAA AAT GAA GAC TAC AGT TCT GAA ATT GAC CAC CTC TCT CTC AAT CAG    96
Glu Asn Glu Asp Tyr Ser Ser Glu Ile Asp His Leu Ser Leu Asn Gln    32

AAG TCC TTC TAT GAT GCA AGC TAT GAG CCA CTT CGT GAG GAC CAG ATG   144
Lys Ser Phe Tyr Asp Ala Ser Tyr Glu Pro Leu Arg Glu Asp Gln Met    48

AAT AAG TTT ATG TCC CTG GAT ACC TCG GAA ACC TCT AAG ACA TCC AAG   192
Asn Lys Phe Met Ser Leu Asp Thr Ser Glu Thr Ser Lys Thr Ser Lys    64

CTT AGC TTC AAG GAG AAT GTG GTG ATG GTG GCA GCC AGT GGG AAG ATT   240
Leu Ser Phe Lys Glu Asn Val Val Met Val Ala Ala Ser Val Lys Ile    80

CTG AAG AAG AGA CGG TTG AGT TTA AAT CAG TTC ATC ACC GAT GAT GAC   288
Leu Lys Lys Arg Arg Leu Ser Leu Asn Gln Phe Ile Thr Asp Asp Asp    96

CTG GAA GCC ATT GCC AAT AAT ACA GAA GAA GAA ATC ATC AAG CCC AGA   336
Leu Glu Ala Ile Ala Asn Asn Thr Glu Glu Glu Ile Ile Lys Pro Arg   112
                              ↓
TCA GCA CAT TAC AGC TTC CAG AGT AAC GTG AAA TAC AAC TTT ATG AGA   384
Ser Ala His Tyr Ser Phe Gln Ser Asn Val Lys Tyr Asn Phe Met Arg   128

GTC ATC CAC CAG GAA TGC ATC CTG AAC GAC GCC CTC AAT CAA AGT ATA   432
Val Ile His Gln Glu Cys Ile Leu Asn Asp Ala Leu Asn Gln Ser Ile   144

ATT CGA GAT ATG TCA GGT CCA TAC CTG ACG GCT ACT ACA TTA AAT AAT   480
Ile Arg Asp Met Ser Gly Pro Tyr Leu Thr Ala Thr Thr Leu Asn Asn   160

CTG GAG GAG GCA GTG AAA TTT GAC ATG GTT GCT TAT GTA TCA GAA GAG   528
Leu Glu Glu Ala Val Lys Phe Asp Met Val Ala Tyr Val Ser Glu Glu   176

GAT TCT CAG CTT CCT GTG ACT CTA AGA ATC TCA AAA ACT CAA CTG TTT   576
Asp Ser Gln Leu Pro Val Thr Leu Arg Ile Ser Lys Thr Gln Leu Phe   192

GTG AGT GCT CAA AAT GAA GAC GAA CCC GTC TTG CTA AAG GAG ATG CCT   624
Val Ser Ala Gln Asn Glu Asp Glu Pro Val Leu Leu Lys Glu Met Pro   208

GAG ACA CCC AAA ATC ATC AAA GAT GAG ACC AAC CTC CTC TTC TTC TGG   672
Glu Thr Pro Lys Ile Ile Lys Asp Glu Thr Asn Leu Leu Phe Phe Trp   224

GAA AAG CAT GGC TCT ATG GAC TAC TTC AAA TCA GTT GCC CAT CCA AAG   720
Glu Lys His Gly Ser Met Asp Tyr Phe Lys Ser Val Ala His Pro Lys   240

TTG TTT ATT GCC ACA AAG CAA GAA AAA TTG GTG CAC ATG GCA AGT GGG   768
Leu Phe Ile Ala Thr Lys Gln Gly Lys Leu Val His Met Ala Ser Gly   256

CCG CCC TCG ATC ACT GAC TTT CAG ATA TTG GAA AAA TAG              804
Pro Pro Ser Ile Thr Asp Phe Gln Ile Leu Glu Lys End              268
```

BOVINE INTERLEUKIN-1α

CROSS-REFERENCE TO RELATED APPLICATION

This is a continuation-in part of application serial no. 07/432,262, filed on Nov. 3, 1989, now abandoned, which is a divisional of application Ser. No. 07/055,108, led on May 28, 198, now U.S. Pat. No. 4,894,333.

BACKGROUND OF THE INVENTION

The present invention relates generally to mammalian cytokines, and particularly to cloning and expression of biologically active mammalian homologues of human IL-1α, e.g., bovine interleukin-1α. Interleukin-1 (IL-1) is the designation given to a family of polypeptides, released by macrophages and certain other cell types in response to immunogenic and traumatic stimulation, which have a primary role in initiating host response to injury and infection. These cytokines have been associated with a complex spectrum of biological activities. IL-1 is a primary immunostimulatory signal capable of inducing thymocyte proliferation via induction of interleukin-2 release, and of stimulating proliferation and maturation of B lymphocytes. In addition, IL-1 has been linked with prostaglandin production and induction of fever, and with promotion of wound healing. Reviews of the literature relating to IL-1 include Oppenheim et al., *Immunol. Today* 7:45 (1986), and Durum et al., *Ann. Rev. Immunol.* 3:263 (1985).

Human IL-1 activity resides in two distantly related proteins, which have been designated IL-1α and IL-1β (March et al., *Nature* 315:641 (1985)). Both molecules are normally synthesized as larger precursors having molecular weights of about 31,000 daltons, which are subsequently processed by proteolytic cleavage to yield mature forms having molecular weights of approximately 17,500 daltons. While the precursor of human IL-1α exhibits IL-1 biological activity, the precursor of human IL-β is biologically inactive, and must be cleaved to provide a mature version having IL-1 activity.

Recently, cDNAs coding for both human IL-1 species have been cloned and expressed in microorganisms, which has enabled production of sufficient quantities of IL-1α and IL-β for preclinical research and potential therapeutic use.

In view of potential therapeutic utility as vaccine adjuvants and components of wound-healing compositions, there is interest in employing bovine IL-1 proteins in veterinary medicine. Therapeutic compositions comprising biologically active quantities of bovine IL-1 proteins or active homologues could be employed to potentiate antibody production in response to vaccine antigens, and also to promote rapid epidermal wound-healing.

SUMMARY OF THE INVENTION

The present invention provides recombinant bovine IL-1α proteins and DNA segments consisting essentially of a single open reading frame nucleotide sequence encoding bovine interleukin-1α (bIL-1α). Preferably, such segments are provided in the form of a synthetic gene which is capable of being expressed in a recombinant transcriptional unit comprising inducible regulatory elements derived from a microbial or viral operon. The present invention also provides recombinant expression vectors comprising the DNA segments, microbial expression systems comprising the recombinant expression vectors, and processes for making the proteins using the microbial expression systems.

BRIEF DESCRIPTION OF THE FIGURES

FIG. 1 indicates the nucleotide sequence of a CDNA clone comprising the coding sequence of bovine IL-1α.

FIG. 2 depicts the nucleotide sequence and derived amino acid sequence of the coding region of the clone depicted in FIG. 1.

DETAILED DESCRIPTION OF THE INVENTION

A DNA segment encoding bovine IL-1α was isolated from a CDNA library prepared by reverse transcription of polyadenylated RNA isolated from bovine alveolar macrophages. A CDNA fragment corresponding to part of the coding sequence of human IL-1α was employed to screen the library by conventional DNA hybridization techniques. Clones which hybridized to the probe were analyzed by restriction endonuclease cleavage, agarose gel electrophoresis, and additional hybridization experiments ("Southern blots") involving the electrophoresed fragments. After isolating several clones which hybridized to the human CDNA probe, the hybridizing segment of one bIL-1α clone was subcloned and sequenced by conventional techniques.

To obtain recombinant protein, a CDNA sequence encoding the polypeptide sequence of mature bIL-1α was inserted into an appropriate expression vector and used to transform a suitable strain of *E. coli*, which was then grown in culture under conditions favoring derepression of the recombinant transcriptional unit. The cultured cells were harvested, and cytosolic protein extracted and tested for expression of bovine interleukin-1 activity in bovine thymocyte proliferation and murine lymphocyte IL-2 production assays.

Alternatively, expression vectors can be assembled comprising synthetic or cDNA-derived DNA fragments encoding bIL-1α or bioequivalent homologues operably linked to inducible elements derived from genes of other bacteria, yeast, bacteriophage, or viruses. Following transformation or transfection of appropriate cell lines, such vectors can be induced to express recombinant protein.

In nucleic acid embodiments, the present invention provides DNA segments consisting essentially of a single open reading frame nucleotide sequence encoding bovine interleukin-1α (bIL-1α). As previously noted, such DNA segments preferably consist essentially of a synthetic gene encoding bIL-1α which is capable of being expressed in a recombinant transcriptional unit comprising inducible regulatory elements derived from a microbial or viral operon. In preferred aspects, the DNA segments comprise at least one, but optionally more than one, sequence component derived from a CDNA sequence or copy thereof. Such sequences may be linked or bounded by DNA sequences prepared by assembly of synthetic oligonucleotides. Exemplary sequences include those substantially homologous to a nucleotide sequence encoding amino acids 120–268 of the polypeptide sequence depicted in FIG. 2. Optionally, the coding sequences may include codons encoding one or more additional amino acids immediately preceding the serine at position 120, for example a codon specifying a glutamine residue or an N-terminal ATG codon specifying methionine linked in reading frame with the nucleotide sequence. Due to code degeneracy, there can be considerable variation in nucleotide sequences encoding the same amino acid sequence; one exemplary DNA embodiment is that corresponding to the sequence of nucleotides 360–804 of FIG. 2. The present invention also provides recombinant expression vectors comprising any of the foregoing DNA segments. The vectors include regulatory elements such as those described in greater detail below.

In process aspects, the present invention provides processes for preparing purified rbIL-1α or a homologue thereof, comprising culturing suitable host/vector expression systems under conditions enabling expression of recombinant protein.

In protein embodiments, the present invention provides polypeptides corresponding to substantially homogeneous bIL-1α, free of contaminating endogenous materials and optionally, without associated native-pattern glycosylation. Such proteins correspond to those encoded by the DNA's of the invention, and include, as one embodiment, N-terminal methionyl bIL-1α. In composition and method-of-use aspects, the present invention provides vaccine adjuvant compositions comprising an effective amount of any of the bIL-α proteins of the invention and a suitable diluent or carrier, and methods for potentiating immune response to antigen in a bovine mammal, comprising administering an effective amount of any of the foregoing compositions. In addition, wound healing compositions are provided, comprising a therapeutically effective amount of any of the bIL-α proteins of the invention and a suitable carrier or vehicle, and methods for promoting wound healing in a bovine mammal, comprising administering a therapeutically effective amount of such compositions. Other immunostimulatory uses and compositions are also contemplated.

Definitions

"Bovine interleukin-1α" and "bIL-1α" refer to a bovine endogenous secretory protein whose biological properties include induction of bovine thymocyte proliferation via induction of IL-2 release, and stimulation of proliferation and maturation of bovine B-lymphocytes. The observed biological properties of the human homologue of bovine IL-1α also include induction of prostaglandin production and provision of a chemotactic signal to fibroblasts. As used throughout the specification, the term "mature bIL-1α" means a bIL-1α protein having bIL-1 biological activity and an amino acid sequence which is substantially homologous to the polypeptide sequence illustrated in FIG. 2, beginning with amino acid 120 and ending with amino acid 268.

"Substantially homologous," which can refer both to nucleic acid and amino acid sequences, means that a particular subject sequence, for example, a mutant sequence, varies from a reference sequence by one or more substitutions, deletions, or additions, the net effect of which do not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents. Generally, homologous DNA sequences can be identified by cross-hybridization under standard hybridization conditions of moderate stringency.

"Recombinant," as used herein, means that a protein is derived from recombinant (e.g., microbial or mammalian) expression systems. "rbIL-1α" means recombinant bIL-1α. "Microbial" refers to recombinant proteins made in bacterial or fungal (e.g., yeast) expression systems. As a product, "recombinant microbial" defines a bovine protein essentially free of native endogenous substances and unaccompanied by associated native glycosylation. Protein expressed in bacterial cultures will be free of polysaccharide; protein expressed in yeast will have a glycosylation pattern different from that expressed in mammalian cells.

"Substantially homogeneous bIL-1α" means a protein composition comprising purified bIL-1α, absent contaminating proteins in quantities detectable by conventional means, for example, staining of polyacrylamide gels. The efficiency of the microbial expression systems disclosed herein permits production of sufficient quantities of bovine IL-1α to provide therapeutically useful quantities of substantially homogeneous material.

"DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in mammalian genes. Sequences of non-translated DNA may be present downstream from the open reading frame, where the same do not interfere with manipulation or expression of the coding regions. "Nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising inducible regulatory elements derived from a microbial or viral operon.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Transcriptional units intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, the cells constituting the system are the progeny of a single ancestral transformant. Recombinant expression systems as defined herein will express heterologous protein upon induction of the regulatory elements linked to the DNA segment or synthetic gene to be expressed.

1. Assays for bIL-1α Biological Activity a. Bovine Thymocyte Mitogenesis Assay

Bovine IL-1α activity can be monitored by a thymocyte mitogenesis assay, which involves ascertaining the capacity of a sample to induce proliferation of thymocytes from freshly killed calves. In this assay, approximately $1.5 \times 10^6$ Ficoll-Hypaque purified bovine thymocytes are dispensed into wells of a flat-bottom microtiter plate (Corning Plastics, Corning, NY, USA) in the presence of a submitogenic concentration of phytohemagglutinin-M (PHA-M) and three-fold serial dilutions of samples to be tested for bIL-1 activity.

Total culture volume per well is 200 microliters. Thymocytes are cultured in RPMI 1640 medium containing 50 U/ml penicillin, 50 μg/ml streptomycin, 2 mM glutamine, 0.2 mM gentamycin, 10 mM HEPES (N-2-hydroxyethylpiperazine-N'-2-ethanesulfonic acid) buffer, pH 7.4, $10^{-5}$ M 2-mercaptoethanol, and 10% (v/v) fetal bovine serum. The samples are incubated for 68 hours at 37° C. in a humidified atmosphere of 5% $CO_2$ in air. Thereafter, cultures are pulsed for approximately 4 hours with 0.5 microcuries (μCi) of tritiated thymidine ($^3$H-Tdr), incubated for an additional 4 hours, and then harvested onto glass fiber filter strips with the aid of a multiple-automated sample harvester. Details of this procedure are provided in U.S. Pat. No. 4,411,992.

In this assay, only cells cultured in the presence of IL-1 incorporate $^3$H-Tdr in a dose-dependent manner. Bovine thymocytes cultured in the absence of IL-1 incorporate only background levels of radiolabel. IL-1 activity is calculated from the linear portion of the $^3$H-Tdr incorporation data. Units of IL-1 activity are determined as the reciprocal dilution of a sample which generates 50% of maximal thymocyte $^3$H-Tdr incorporation in a given assay. If desired, standard solutions of purified recombinant human IL-1β at a concentration of can be employed for reference purposes.

b. IL-1 Conversion Assay

Alternatively, IL-1 activity can be assayed by an IL-1 conversion assay, which is based upon the observation that bIL-1 proteins induce certain IL-1-dependent IL-2-producing cell lines, for example, the murine T-cell line LBRM-33-1A5 (ATCC CRL-8079) to produce IL-2. IL-1 conversion assays are described by Conlon, *J. Immunol.* 131:1280 (1983) and Loventhal et al., *J. Immunol.* 137:1226 (1986). In these assays, cells to be induced are first inactivated by treatment with 50 μg/ml mitomycin C and then incubated in the presence of a suboptimal mitogenic concentration of PHA-M, varying dilutions of sample, and IL-2 dependent cells, for example the murine T-cell line CTLL-2 (ATCC TIB 214). Only the IL-2 dependent cells added to wells previously contacted with IL-1 (thereby inducing IL-2 production by the inactivated cells) will proliferate and incorporate radiolabel. Conversion assays of this type are both more rapid and more sensitive than the thymocyte mitogenesis assay.

In a preferred conversion assay, approximately $5 \times 10^4$ inactivated EL4-6.1 cells (a clone derived from the murine EL4 cell line, ATCC TIB 39) are dispensed into wells of a flat-bottom microtiter plate containing serial threefold dilutions of samples to be tested for activity. Cells are cultured in a total volume of 100 microliters of complete Clicks medium containing 50 U/ml penicillin, 50 μg/ml streptomycin, 2 mM glutamine, 0.2 mM gentamycin, 10 mM HEPES buffer, pH 7.4, $10^{-5}$ M 2-mercaptoethanol, and 10% (v/v) fetal bovine serum.

The samples are incubated for 24 hours at 37° C. in a humidified atmosphere of 5% $CO_2$ in air. At this point, approximately $4 \times 10^3$ washed CTLL-2 cells are added and incubation continued for an additional 20 hours. Finally, cultures are pulsed for approximately 4 hours with 0.5 microcuries (μCi) of tritiated thymidine ($^3$H-Tdr), incubated for an additional 4 hours, and the resulting pulsed cultures assayed for thymidine incorporation as detailed above.

Protein and Endotoxin Assays

Protein concentrations can be determined by any suitable method. However, the Bio-Rad total protein assay (Bio-Rad Laboratories, Richmond, Calif., USA) is preferred. SDS-PAGE can also be employed to monitor purification progress, substantially as described by Kronheim et al., *J. E Med.* 161:490 (1985), or other suitable techniques. Additional details regarding use of variants of the IL-1 assays described above are disclosed by Conlon, *J. Immun.* 131:1280 (1983) and Kronheim et al., supra.

Endotoxin levels in protein compositions are conveniently assayed using a commercial kit available from Whittaker Bioproducts, Walkersville, Md., U.S.A., (Quantitative Chromogenic LAL OCL-1000) or its equivalent. This method uses a modified Limulus amebocyte lysate and synthetic color-producing substrate to detect endotoxin chromogenically. Purified recombinant bIL-1α is tested for presence of endotoxin at multiple dilutions. The assay is preferably performed shortly following completion of purification and prior to storage at −70° C. To minimize the possibility of bacterial contamination during the purification process itself, sterile buffers should be employed.

The Native bIL-1α Sequence

The nucleotide sequence of a CDNA clone isolated from a bovine alveolar macrophage library is set forth in FIG. 1. The initiator methionine (at nucleotide 55), first codon of mature bIL-1α (at nucleotide 412) and stop codon (at nucleotide 859) are underlined.

FIG. 2 indicates the CDNA and deduced amino acid sequences of the coding region of the bIL-1α clone fully set forth in FIG. 1. As in the case of human IL-1α, bIL-1α is apparently translated in vivo as a precursor protein of approximately 31,000 dalton molecular weight, which is subsequently processed by an endogenous protease or proteases to provide the mature form, which has a predicted molecular weight of about 17,500 daltons. In FIG. 2, nucleotides and amino acids are numbered beginning with the initiator methionine of the precursor. One variant of the mature sequence, which is underlined, begins with a AGT codon specifying the serine residue indicated by an arrow at residue 120. The predicted amino acid sequence of bIL-1α includes an Asn-Gln-Ser sequence at the residues marker 141–143 in FIG. 2 which provides a potential N-linked glycosylation site.

A recombinant DNA segment encoding the amino acid sequence of bIL-1α can be obtained by screening of appropriate cDNA libraries using appropriate probes, or by assembly of artificially synthesized oligonucleotides.

Construction of expression vectors

Mature bIL-1α can be expressed in bacteria, yeast, mammalian, or other cells under the control of appropriate inducible promoters.

Appropriate expression vectors for bacterial use are constructed by inserting the heterologous structural DNA sequence encoding bIL-1α together with translational initiation and termination signals in operable reading phase with a functional promoter. The vector will comprise one or more phenotypic selectable markers and an origin of replication to ensure amplification within the host. Optionally, the heterologous sequence can be integrated into the vector such that it is translated as a fusion protein, in conjunction with an identification peptide (e.g., DYKDDDDK) or other sequence imparting desired characteristics relating to stabilization or purification of expressed protein. Suitable prokaryotic hosts for transformation include *E. coli, Bacillus subthis, Salmonella typhimurium,* and various species within the genera *Pseudononas, Streptomyces,* and Staphylococcus, although others may also be employed as a matter of choice.

Appropriate cloning and expression vectors for use with numerous bacterial, fungal, and yeast hosts are described by Pouwels, et al., *Cloning Vectors: A Laboratory Manual,* (Elsevier, N.Y., 1985), the relevant disclosure of which is hereby incorporated by reference.

As a representative but nonlimiting example, useful expression vectors for bacterial use can comprise a selectable marker and bacterial origin of replication derived from commercially available plasmids derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wisc., USA). These "backbone" sections are combined with an appropriate promoter and the structural sequence to be expressed.

A particularly useful bacterial expression system employs the phage λ $P_L$ promoter and cI857ts thermolabile repressor. Plasmid vectors available from the American Type Culture Collection which incorporate derivatives of the X P promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al., *J. Mol. Biol.* 189:113 (1986), the lacz promoter described by Lauer, *J. Mol. Appl. Genet.* 1:139-147 (1981) and available as ATCC 37121, and the tac promoter described by Maniatis, *Molecular Cloning: A Laboratory Manual* (Cold Spring Harbor Laboratory, 1982, p 412) and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification.

Yeast systems, preferably employing *Saccharomyces cerevislae,* may also be used for expression of the recombinant proteins of this invention. Other species, for example, Pichia or Kluyveromyces, have also been employed as production strains for recombinant proteins.

Generally, useful yeast vectors will include origins of replication and selectable markers permitting transformation of both yeast and *E. coli,* e.g., the ampicillin resistance gene of *E. coli* and yeast TRP1 gene, and a promoter derived from a highly-expressed yeast gene to induce transcription of a downstream structural sequence. Such promoters can be derived from yeast operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the extracellular medium.

Useful yeast vectors can be assembled using DNA sequences from pBR322 for selection and replication in *E. coli* ($Ap^r$ gene and origin of replication) and yeast DNA sequences including a glucose-repressable alcohol dehydrogenase 1 or 2 (ADH1 or ADH2) promoter. The ADH2 promoter has been described by Russell et al., *J. Biol. Chem.* 258:2674 (1982) and Beier et al., *Nature* 300:724 (1982). Such vectors may also include a yeast TRP1 gene as a selectable marker and the yeast 2μ origin of replication. A yeast leader sequence, for example, the α-factor leader, enabling secretion of heterologous proteins from a yeast host, can be inserted adjacent to the promoter and translation initiation sequence and in phase with the structural gene to be expressed. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen, et al., *Proc. Natl. Acad. Sci. USA* 75:1929 (1978), selecting for $Trp^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADHL or ADH2 promoters are grown for expression in a rich medium consisting of 1% yeast extract, 2% peptone, and 1% glucose supplemented with 80 μg/ml adenine and 80 μg/ml uracil. Derepression of the ADH1 and ADH2 promoters occurs upon exhaustion of medium glucose. Crude yeast supernatants are harvested by filtration and frozen or held at 4° C. prior to further purification.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences.

DNA sequences derived from the SV40 viral genome, for example, SV40 origin, early promoter, enhancer, splice, and polyadenylation sites may be used to provide the required nontranscribed genetic elements.

Microbial Expression and Protein Purification

The general purification scheme described herein involves an initial acid extraction from cell pellets, followed by ion exchange chromatography in aqueous media. The ion exchange chromatography may comprise cation exchange chromatography followed by anion exchange chromatography.

Microbial cells employed in expression of rbIL-1α can be disrupted by any convenient method, including freeze-thaw cycling, sonication, mechanical disruption, or use of cell lysing agents. Preferably, the acid-mediated extraction step for rbIL-1α is conducted in an aqueous buffered medium having a pH from about 2.0 to about 4.0, and most preferably, at a pH from about 2.5 to about 3.5. Generally, the initial acid extraction steps are coupled with subsequent chromatography in aqueous media. This part of the purification process preferably includes an initial ion exchange chromatography stage, optionally followed by one or more size-exclusion chromatography, affinity chromatography, or HPLC steps. The ion exchange stage comprises, in a preferred aspect, cation exchange chromatography followed by anion exchange chromatography.

Suitable cation exchange chromatography media include various insoluble matrices comprising sulfopropyl or carboxymethyl groups. Sulfopropyl groups are preferred. The matrices can be acrylamide, agarose, dextran, cellulose or other ion exchange resins or substrates commonly employed in protein purification. A particularly useful material for cation exchange chromatography of rbIL-1α is Sulphopropyl Sephadex C-25 (Pharmacia Fine Chemicals, Uppsala, Sweden). When media containing sulfopropyl groups are employed, extracts containing rbIL-1α are applied at a pH from about 2.5 to about 5.0, preferably about 4.0, in a suitable buffer such as sodium citrate. rIL-1α species are bound by the ion exchanger, and can be eluted in more highly purified form by application of a weakly basic eluant having a pH from about 7.5 to about 9.0, for example, 10 mM Tris-HCl, pH 8.1.

Suitable anion exchange chromatography media include various insoluble matrices comprising diethylaminoethyl (DEAE) or diethyl-(2-hydroxypropyl)aminoethyl (QAE) groups. DEAE groups are preferred. The matrices can be acrylamide, agarose, dextran, cellulose or other types commonly employed in protein purification. A particularly useful material for cation exchange chromatography of rbIL-1α is DEAE-Sephacel (Pharmacia). When media containing DEAE groups are employed, extracts containing rbIL-1α are applied at a weakly basic pH. For example, the pooled rbIL-1α-containing fractions resulting from the previous cation exchange chromatography step (at a pH of about 8.1) can be applied directly in a suitable buffer such as Tris-HCl. rbIL-1α species are bound by the anion exchange media, and can be eluted in more highly purified form by application of a salt gradient in the same buffer. Generally, the characteristics of the gradient can be determined by preliminary elution experiments involving a small quantity of recombinant protein. By comparison, recombinant human IL-1α is known to elute from DEAE-Sephacel at 0.17–0.22 M NaCl.

Experiments in which the pH of the initial extraction buffer was varied have indicated that extraction of recombinant human IL-1α from E. coli is optimally performed under acid conditions, for example, pH 2.5–3.5 in order to precipitate unwanted proteins while solubilizing rhIL-1α. The optimal pH for the initial extraction step of rbIL-1α may vary from the human protein, or between fermenter batches. For this reason, small-scale pilot runs may be employed to determine optimal pH, particularly where large quantities of material are involved.

As noted previously, rbIL-1α can be efficiently produced by growth and derepression of appropriate E. coli cells harboring thermoinducible high level expression plasmids. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al., Proc. Natl. Acad. Sci. USA 82:88 (1985), optionally including antibiotics, derepressed at a cell density corresponding to $A_{600}=0.4–0.5$ by elevating the temperature to 42° C., and harvested from 2–20, preferably 3–6, hours after the upward temperature shift. The cell mass is initially concentrated by filtration or other means, then centrifuged at $10,000 \times g$ for 10 minutes at 4° C. followed by rapid freezing the cell pellet.

To achieve the initial acid extraction, cell pellets are suspended in 30 mM Tris-HCl buffer, pH 8, containing 5 mM EDTA and 1 mM phenylmethylsulfonyl fluoride (PMSF). The resulting suspension is rapidly frozen in a dry ice/methanol bath and then thawed. Next, 30 mM sodium citrate buffer at pH 3.0, containing 5 mM EDTA, is added to the suspensions and cells are disrupted using a cell homogenizer. The resulting acid suspensions are incubated for 60 minutes in a 37° C. water bath. Following incubation, the extracts are rapidly frozen in a dry-ice/methanol bath, thawed, and then centrifuged at 4° C. for 45 minutes at $38,000 \times g$. Supernatants are then decanted for use in the next purification step.

Extraction of rbIL-1α from E. coli cell suspensions at pH 3.0 results in precipitation of most contaminating proteins and significant recovery of rbIL-1α activity. Extracts containing rbIL-1α can be adjusted to pH 4.0 by appropriate buffer and applied to an SPS C-25 column pretreated with 0.1% Triton X-100 (polyoxyethylene ether; Sigma Chemical Company, St. Louis, Missouri, USA) and 10% fetal calf serum. The column can then be washed with 3 column volumes of 10 mM 2-(N-morpholino)ethanesulfonic acid (MES) buffer, pH 5.0, and protein eluted from the column with 10 mM Tris-HCl, pH 8.1.

Fractions containing bIL-1 activity from the SPS step can then be combined and applied to columns containing DEAE-Sephacel previously equilibrated with 10 mM Tris-HCl, pH 8.1. The DEAE columns are washed with additional starting buffer to elute bIL-1α which is substantially pure by SDS-PAGE.

The foregoing ion exchange chromatography procedures can be repeated to attain further purification, or combined with subsequent size exclusion chromatography or high-performance liquid chromatography (HPLC) steps to attain a final product of high relative purity.

Administration of IL-1

In use, purified bovine IL-1α is administered to a mammal for treatment in a manner appropriate to the indication. Thus, for example, bIL-1α administered as a vaccine adjuvant will be given in conjunction with or shortly following administration of an appropriate vaccine antigen. Administration may be by injection, continuous infusion, sustained release from implants, or other suitable technique. Where bIL-1α is administered as an aid to wound healing, it will typically be applied topically to the site of injury, for example, in conjunction with a wound dressing. Typically, bIL-1α will be administered in the form of a composition comprising purified protein in conjunction with physiologically acceptable carriers, excipients or diluents. Neutral buffered saline or saline mixed with conspecific serum albumin are exemplary appropriate diluents.

EXAMPLE 1

Isolation of CDNA encoding bIL-1α and Bacterial Expression of Active Protein

A CDNA polynucleotide probe was prepared from an 847 base pair (bp) PstI/HincII fragment of the structural sequence of a human IL-1α CDNA by nick-translation using DNA polymerase I. The method employed was substantially similar to that disclosed by Maniatis et al., supra, p. 109.

A CDNA library was constructed by reverse transcription of polyadenylated MRNA isolated from total RNA extracted from bovine alveolar macrophages (BAM). BAM were cultured in RPMI 1640 medium plus 10% fetal bovine serum for 16 hours with 10 μg/ml *Salmonella typhimurium* lipopolysaccharide (LPS) in order to elicit maximal IL-1 specific messenger RNA production. The CDNA was rendered double-stranded using DNA polymerase I, blunt-ended with T4 DNA polymerase, methylated with EcoRI methylase to protect EcoRI cleavage sites within the CDNA, and ligated to EcoRI linkers. The resulting constructs were digested with EcoRI to remove all but one copy of the linkers at each end of the CDNA, and ligated to EcoRI-cut and dephosphorylated arms of bacteriophage λgt10 (Huynh et al., *DNA Cloning: A Practical Approach*, Glover, ed., IRL Press, pp. 49-78). The ligated DNA was packaged into phage particles using a commercially available kit to generate a library of recombinants (Stratagene Cloning Systems, San Diego, Calif., USA 92121). Recombinants were plated on *E. coli* strain C600(hf1−) and screened by standard plaque hybridization techniques under conditions of moderate stringency (60° C., 6xSSC). Following several rounds of screening, four clones were isolated from the library which hybridized to the CDNA probe. The clones were plaque purified and used to prepare bacteriophage DNA which was digested with EcoRI. The digests were electrophoresed on an agarose gel, blotted onto nylon filters, and retested for hybridization. The clones were digested with EcoRI followed by preparative agarose gel electrophoresis, then subcloned into an EcoRI-cut derivative (PGEMBL) of the standard cloning vector pBR322 containing a polylinker having a unique EcoRI site, a BamH1 site and numerous other unique restriction sites. An exemplary vector of this type is described by Dente et al., *Nucleic Acids Research* 11:1645 (1983). Restriction mapping indicated the presence of an insert of approximately 2.1 kilobases (kb) in one of the clones. This insert was subcloned and sequenced. Clone bovIL-1α 7.4 included a DNA segment encoding a protein of 268 amino acids having a predicted molecular weight of 31 kilodaltons (Kd) and bearing approximately 72% homology to human IL-1α.

A bacterial expression vector can be constructed by digesting the cloning vector including the bIL-1α sequence with BsmI and PstI, and isolating the resulting 1080 bp fragment encoding mature bIL-1α. This fragment is then ligated to the following oligonucleotide polylinker:

<u>ClaI</u>
```
C GAT ACT ATG TCT AAC GTA AAA TAT AAC TTT
  TA TGA TAC AGA TTG CAT TTT ATA TTG AAA
         Met Ser Asn Val Lys Tyr Asn Phe
```

```
                                         BsmI
ATG AGA GTA ATT CAT CAA GAA TGC A
TAC TCT CAT TAA GTA GTT CTT A
Met Arg Val Ile His Gln Glu Cys
```

The resulting construct is ligated into ClaI- and PstI-cut pPL3 for thermoinducible expression in an appropriate host strain, e.g., *E. coli* K802 (pRK248cIts; ATCC 33526). pPL3 is a derivative of pBR322 comprising a version of the phage λ $P_L$ promoter previously described. Following expression, a crude SDS extract of bacteria comprising the bIL-1α expression vector can be assayed by the bovine thymocyte proliferation assay to confirm biological activity. Additional quantities of purified recombinant protein can be obtained from acid extracts as previously described.

EXAMPLE 2

Expression of bIL-1α in a Yeast System

The coding region of the bIL-l(X gene is removed from an appropriate CDNA clone or assembled from synthesized oligonucleotides and inserted into a bacterial/yeast shuttle vector, pYADH (ATCC 39967) as detailed below. The resulting expression vector is amplified in *E. coli* host cells and then employed to transform yeast host cells for expression of recombinant protein under the control of the yeast ADH1 promoter.

A plasmid comprising the coding region of the bIL-1α gene is first cleaved at a PstI site located in the 3′ flanking region of the gene. Using S1 nuclease, the PstI site is blunt-ended to provide a suitable terminus for ligation to the StuI site of plasmid pYADH. The resulting blunt-ended linear fragment is then cut with the restriction endonuclease BsmI to provide a fragment comprising the major portion of the coding region of the bIL-1α gene.

A synthetic oligonucleotide is chemically synthesized to add back the 5′ terminal portion of the coding region of the bIL-1α gene and also to create a translation initiation codon at the 5′ end of the coding region. The composition of the oligonucleotide, as shown below, includes an EcoRI cohesive5′ terminal followed by an ATG initiation codon and then the5′ end of the coding region of the IL-1 gene up to and including a BsmI site.

<u>EcoRI</u>
```
AATTCAAC ATG TCT AAC GTA AAA TAT AAC TTT
    GTTG TAC AGA TTG CAT TTT ATA TTG AAA
         Met Ser Asn Val Lys Tyr Asn Phe
```

-continued

```
                                      BsmI
ATG AGA GTA ATT CAT CAA GAA TGC A
TAC TCT CAT TAA GTA GTT CTT A
Met Arg Val Ile His Gln Glu Cys
```

The pYADH expression vector is prepared for ligation to the synthetic oligonucleotide and the excised major portion of the coding region of the bIL-1α gene by digestion of the vector to completion with the restriction endonucleases EcoRI and StuI by standard techniques, as set forth in Maniatis et al., supra at 104. The desired larger fragment from the digestion is isolated by electrophoresis on 0.7% agarose gel at 100 volts at 22° C. for two hours.

The synthetic DNA oligomer, the excised major portion of the coding region of the bIL-1α gene and the desired linearized pYADH fragment are ligated together in a reaction mixture composed of 1 μg/ml of the pYADH vector fragment (EcoRI - StuI), 0.4 μg/ml of the major bIL-1 α DNA fragment (BsmI, PstI [blunt]), 0.005 μg/ml of synthetic oligonucleotide (EcoRI - BsmI), and 50 units/ml of T4 DNA ligase in sufficient T4 DNA ligase buffer (10x T4 DNA ligase buffer is 0.4 M Tris [pH 7.4] 0.1 MgCl₂, 0.1 M dithiothreitol, 10 mM spermidine, 10 mM ATP and 1 mg/ml BSA) to form a 20 μl reaction volume. The reaction is carried out by incubation at 15° C. for 15 hours.

The resulting recombinant plasmid is then used to transform E. coli strain RR1 using standard techniques. The host cells are grown in culture to amplify plasmid DNA, which is isolated by a standard method, e.g., as detailed by Maniatis et al., supra at 368. Plasmid DNA is purified by centrifugation to equilibrium in cesium chloride-ethidium bromide density gradients, and then employed to transform a protease-deficient yeast strain (e.g., 2OB-12 (α, PEP 4.3, TRP1) of S. cerevisiae by standard techniques, such as those disclosed in published European Patent Application EPA 0165654, selecting for tryptophan prototrophs.

For expression of recombinant protein, yeast transformants are inoculated from minimal medium into rich medium (1% yeast extract, 2% peptone, 2% glucose) and grown at 30° C. for 15-20 hours until the late exponential phase. At harvest, the protease inhibitor phenyl methyl sulfonyl fluoride (PMSF) is added to a concentration of 1 mM. The culture is then centrifuged at 400×g to pellet cells, which are washed once in 0.1 vol. cold H₂O, resuspended in 0.01 vol. cold H₂O containing 1 mM PMSF and vortexed with glass beads (1/3 vol.) for 2 minutes. The cell debris and glass beads are pelleted by centrifugation. The resulting supernatant is then assayed for the presence of recombinant protein by bovine thymocyte proliferation and IL-1 conversion assays.

What is claimed is:

1. Substantially homogeneous purified bovine interleukin-1α (bIL-1α).

2. Purified bIL-1α according to claim 1, wherein the molecular weight of a full length precursor form of said bIL-1α is about 31 kilodaltons as calculated from the amino acid sequence.

3. Purified bIL-1α according to claim 1, wherein said bIL-1α is mature bIL-1α.

4. Purified bIL-1α according to claim 3, wherein the amino terminus of said mature bIL-1α comprises an amino acid sequence selected from the group consisting of Met—Ser—Asn—Val—Lys—Tyr—Asn—Phe—Met—Arg—Val—Ile—His—Gln—Glu—Cys— and Ser—Asn—Val—Lys—Tyr—Asn—Phe—Met—Arg—Val—Ile—His—Gln—Glu—Cys—.

5. A pharmaceutical composition comprising a therapeutically effective amount of purified bIL-1α according to claim 1 and a diluent or carrier.

6. A vaccine adjuvant composition comprising an effective amount of bIL-1α according to claim 1 and a suitable diluent or carrier.

7. A method for potentiating an immune response to an antigen in a bovine mammal, comprising administering an antigen to said bovine mammal and also administering an effective amount of a composition according to claim 6.

8. A pharmaceutical composition comprising a therapeutically effective amount of bIL-1α according to claim 3 and a diluent or carrier.

9. A vaccine adjuvant composition comprising an effective amount of bIL-1α according to claim 3 and a suitable diluent or carrier.

10. A method for potentiating an immune response to an antigen in a bovine mammal, comprising administering an antigen to said bovine mammal and also administering an effective amount of a composition according to claim 9.

* * * * *